United States Patent [19]

Schepers et al.

[11] Patent Number: 5,204,106
[45] Date of Patent: Apr. 20, 1993

[54] PROCESS FOR RESTORING AN OSSEOUS DEFECT OR DEFICIENCY BY FILLING WITH OSSEOUS TISSUE

[75] Inventors: Evert Schepers, Leuven, Belgium; Paul Ducheyne, Bryn Mawr, Pa.; Raymond Kempeneers, Mol, Belgium

[73] Assignee: FBFC International S.A., Brussels, Belgium

[21] Appl. No.: 511,303

[22] Filed: Apr. 19, 1990

[30] Foreign Application Priority Data

Apr. 20, 1989 [FR] France ................. 89 05504

[51] Int. Cl.⁵ .............................................. A61F 2/28
[52] U.S. Cl. ..................... 424/423; 424/422; 623/16
[58] Field of Search ............. 424/422, 423; 623/16

[56] References Cited

U.S. PATENT DOCUMENTS

| | | | |
|---|---|---|---|
| 3,905,047 | 9/1975 | Long | 623/16 |
| 3,981,736 | 9/1976 | Broemer et al. | 623/16 |
| 4,563,350 | 1/1989 | Nathan et al. | 424/95 |

FOREIGN PATENT DOCUMENTS

| | | | |
|---|---|---|---|
| 0112319 | 6/1984 | European Pat. Off. | 623/16 |
| 3306648 | 9/1983 | Fed. Rep. of Germany | 424/423 |
| 3242263 | 10/1988 | Japan | 623/16 |

*Primary Examiner*—Page: Thurman K.
*Assistant Examiner*—Carlos Azpuru
*Attorney, Agent, or Firm*—Dennison, Meserole, Pollack & Scheiner

[57] ABSTRACT

Process for the restoration of an osseous defect or deficiency by filling with osseous tissue with the aid of a bioreactive granular material causing an osteostimulation, the particles of said granular material being disintegrated from the inside, dissolved and replaced by osseous tissue, the granular material containing 40 to 55% $SiO_2$, 10 to 32% $Na_2O$, 0 to 12% $P_2O_5$ and 10 to 32% CaO, which has a grain size distribution between 280 and 425 µm, sharp edges, an irregular profile and surface microdefects or microcracks.

8 Claims, 3 Drawing Sheets

PROCESS FOR RESTORING AN OSSEOUS DEFECT OR DEFICIENCY BY FILLING WITH OSSEOUS TISSUE

TECHNICAL FIELD

The invention relates to a process for the rapid and complete filling of an osseous deficiency by the formation of osseous tissues with the aid of a granular material.

PRIOR ART

It is known that products such as dense or porous hydroxylapatite, tricalcium phosphate and bioglasses can be used in granular form for filling osseous lesions such as periodontal pockets, extraction sites, cystic lesions, osseous deficiencies, etc.

When filling osseous cavities, such granular materials and in particular hydroxylapatite acts as a matrix for the purpose of restoration by osseous or bone growth (i.e. normal proliferation of osseous cells). Thus, it has been demonstrated that an osteoconduction occurs (i.e. a growth of osseous tissues along the surface of implanted granules) and a progressive filling of the intergranular space. Unfortunately this intergranular growth is generally limited to the particles located in the immediate vicinity of the walls of the osseous cavity, the other particles being surrounded by fibrous tissues, so as to give a solid mass. Thus, osteoconduction leads to particles which are progressively coated by osseous tissue, which proliferates from the walls of the osseous cavity, an optimum reaction of the particles only taking place on the surface.

Moreover, when said particles are placed in a cavity, e.g. an extraction site, they can migrate into adjacent soft tissues and are fixed at inappropriate points. This can lead to complications such as dysesthesia or paresthesia of the nerve, pain, infection, perforation of the gum and loss of particles.

Therefore the development of the use of particles, such as hydroxylapatite particles, has been directed at improving their properties of putting into and maintaining in place. This can be obtained by putting into place with the aid of resorbable envelopes, adhesives, collagen or its derivatives, adhesive fibrins, etc.

Thus, the filling of the cavity becomes, after osteoconduction, a composite of fibrous, osseous tissues and apatite or bioglass, which has inadequate mechanical properties inferior to those of the bone. For example, the insertion of prosthetic implants into such a composite is not generally possible, because it may suffer from time rigidity, stability or compatibility deficiencies. Moreover, the presence of particles in adjacent tissues is not desirable.

European application 0206726 relates to the repair of periodontal defects (pockets located between the jawbone and the root of teeth) by putting into place in said defect a bioactive granular material and illustrates the obtaining of such a bone-granular material composite by osteoconduction, i.e. intergranular growth of the osseous tissue from the osseous walls of the defect (p 15, lines 13 to 15 and 25 to 28). The said granular material also has individual inherent characteristics (chemical nature, selection of a granulometric pile), which make it possible to obtain certain advantages in accordance with the main sought objective, such as a good cohesion facilitating its putting into and maintaining in place in the defect, together with a stopping action making it possible to stop the blood flow occurring in the defect. This particular granular material is obtained by a process consisting of melting a mixture of powders followed by pouring into water in the form of frits, which are washed with acetone and then ground prior to granulometric selection.

The granular material described in the above document to some extent serves as a permanent implant, the object of an osteoconduction and is therefore progressively coated with osseous tissues, which adhere to said implant and keep it firmly in place. The repair of such a periodontal defect, leading to said bone-glass composite, does not have special requirements with regards to the mechanical characteristics, because it is not generally intended to receive a subsequent prosthesis implantation.

In order to obviate the disadvantages resulting from an osteoconduction from the osseous walls of a cavity into an intergranular space and leading to said bone-granular material composites, the Applicant has attempted to fill the osseous defects by osseous tissues and to increase the speed with which said osseous tissues are formed. The Applicant has also sought to produce an osteostimulation, defined as being an osteogenesis in an osseous site without contact with the adjacent bone, osteogenesis being the phenomenon leading to osseous tissue. Another objective is to improve the mechanical characteristics of the osseous tissue filling said defect or deficiency, so that subsequently successful prosthesis implantations can take place there.

DESCRIPTION OF THE INVENTION

The invention consists of forming osseous tissue in order to fill an osseous defect or deficiency by putting into place in the latter a bioreactive granular material, which leads to osteogenesis by osteostimulation, the constituent particles of said granular material being progressively disintegrated from the inside, in order to bring about a differentiation of the precursor cells into osteoblasts, followed by dissolving and rapid replacement by the osseous tissue.

The procursor cells are mesenchymal cells initially present in the biological medium, which can be differentiated into fibroblast and chondroblast cells depositing fibrous or cartileginous tissues (to be avoided in the present invention) and into osteoblast cells which deposit osseous tissue (sought in the present invention).

It is important to control the disintegration and dissolving of the granular material, because if said phenomena are not controlled, they could e.g. give rise to an excessively intense inflammation, which would prevent the appearance of conditions favourable to the differentiation of the mesenchymal cells into osteoblasts. Moreover, an excessively fast dissolving of the granules compared with the osseous tissue formation rate would no longer lead to the formation of said osseous tissues and would instead lead to the formation of undesired fibrous tissues.

Thus, the constituent particles are disintegrated from the inside, disappear and are progressively and rapidly replaced by osseous tissue rather than by fibrous tissue. Following the disappearance of the material, an osseous mass is obtained which leads itself perfectly e.g. to the subsequent prosthesis implantations. This granular material is also easy to use and apply. Its particles are readily maintained in place in the defect or deficiency without having to use additional means.

According to the invention, the granular material for filling the osseous deficiency in the form of particles is characterized in that said particles have, in combination, the following composition (in % by weight):
$SiO_2$ between 40 and 53%
$Na_2O$ between 10 and 32%
$P_2O_5$ between 0 and 12%
$CaO$ between 10 and 32%,
a grain size distribution such that at least 95% of them have a size between 280 and 425 $\mu$m, sharp edges, an irregular profile and surface microdefects or microcracks.

It is important that the bioreactive glasses used do not contain fluorinated products. They generally contain $SiO_2$, $Na_2O$, $P_2O_5$, an alkaline earth oxide such as $CaO$. The presence of boron and alumina is not desired.

The presence of fluorinated products such as $CaF_2$ is prejudicial, because it excessively slows down restoration and, with certain grain sizes, can also lead to an excessively intense inflammatory reaction.

The composition of the glass is preferably within the following ranges:

| | |
|---|---|
| $SiO_2$ | 42–48 |
| $Na_2O$ | 14–28 |
| $P_2O_5$ | 0–10 |
| $CaO$ | 20–29 |

As has been stated the disintegration and dissolving of the particles must be well controlled and on the basis of a very narrow grain size distribution of the particles the size must be between 280 and 425 $\mu$m, i.e. 95% of the powder must be held back on a screen whose mesh opening or size is equal to the recommended lower limit and 95% of the same powder must pass through a screen, whose mesh opening or size is equal to the recommended upper limit.

It is advantageous that within the grain size fraction of 280 to 425 $\mu$m, ⅔ of the particles must be included in a 300 to 360 $\mu$m fraction, the best results being obtained with a fraction containing at least 90% of particles between 300 and 360 $\mu$m.

The material must be in the form of powder constituted by angular particles having sharp edges and an irregular profile. The constituent particles must have surface microdefects or microcracks. These microdefects or microcracks form the start of small ducts which, as will be shown hereinafter, connect the interior of the particles to the exterior and favour their disintegration from the inside.

These size and morphology characteristics are essential for allowing the use of the above-described bioglasses with the sought results.

In general, the particles according to the invention have been implanted in dogs and then samples were taken 1, 2, 3, 6 and 12 months following the fixation treatment, were cut up with the section cutter and prepared for observation by microscopy and then analyzed.

With a material according to the invention, the Applicant has found that, not only does the osseous tissue develop from the osseous cavity wall by osteoconduction and accompanied by the formation of an osseous skeleton, but unexpectedly the particles in the centre of the cavity, i.e. having no contact with the walls, disintegrate and ossify simultaneously from their centre, said disintegration leading to no harmful chronic inflammatory reaction.

Within said particles, an excavation occurs by disintegration and dissolving of the central part under the action of the physiological liquid and lymphocyte, plasmocyte, histiocyte and macrophage cells. These central excavations are connected to the exterior by small ducts. Over the wall of the excavation formed extends osseous tissue covered by an osteoid tissue coating and a band of active osteoblast cells. Thus, the desired differentiation has taken place, but unexpectedly of mesenchymal cells into osteoblasts rather than fibroblasts. A considerable number of these excavations were already practically filled with osseous tissue after three months. There is no direct link between the osseous tissue developing in the centre of the particles and the external osseous tissue.

An explanation can be that the implanted particles are exposed to the action of the physiological liquid and cells. The latter bring about a dissolving and penetrate the interior of said particles via surface defects or microcracks, due to the process used for the production of the granular material and which are accessible to said liquid. Local glass composition and pH changes occur, which are favourable to osteostimulation, which favours the preferred transformation of precursor mesenchymal cells into osteoblasts depositing osseous tissue. In particular, there is no development of fibroblast cells, which generate prejudicial fibrous tissues, in contact with the glass which has reacted. The interior of the particles constitutes a highly protected medium, which makes it possible to create and maintain said conditions favourable to the differentiation of the mesenchymal cells into osteoblasts. This means that the filling granular material is osteostimulating under the limited, specific conditions of the invention. In particular the excessively small particles give a too intense reaction and lead to fibrous tissues, said conditions being unfavourable to the differentiation of mesenchymal cells into osteoblasts.

Thus, at the end of development, in the osseous deficiency is obtained an osseous filling material, which is organically connected to the wall of the defect. Thus, this filling has the properties of the bone and can be used under the same conditions as the adjacent bone.

Moreover, there is no migration of particles into the non-osseous tissues adjacent to said osseous defect.

The material according to the invention is active and not stable. It has a stimulating action and unexpectedly leads to the formation of osseous tissue by osteostimulation. Thus, it makes it possible to obtain a much faster ossification, because it takes place not only from the wall of the cavity by coating the particles, but also and simultaneously in the mass by the interior of the particles.

The size and morphology characteristics are essential for obtaining the sought results. Thus, when the particles are brought into contact with the physiological medium, a calcium phosphate-rich surface layer (CaP) is formed, whereas the underlying layer becomes rich in $SiO_2$.

If the particles are too small, their interior is constituted by a silica gel covered with an excessively thin and very fragile CaP layer, which has a tendency to break. The macrophage cells absorb the silica and the particles disappear too rapidly without the medium, which is very protected and favourable to the differentiation of the precursor cells into osteoblasts, constituted by the internal excavation of the particle, having time to form and give rise to the osseous tissue. No osteostimulation occurs with this type of particle.

In the same way, if in a particular grain size fraction said excessively small particles are present in an excessive quantity, the too intense reaction which they bring about can lead to an inhibition of osteostimulation, which could occur with larger particles.

If the particles have a grain size distribution in accordance with the invention, the CaP layer is more solid and stable and the centre contains silica, but no glass. As the CaP no longer breaks, the macrophage cells can penetrate the particle by microdefects and create the excavation. The highly protected and differentiation-favourable medium can then develop and osteogenesis takes place by osteostimulation.

It the particles are too large, glass remains within said particles. There is no excavation formation and consequently the desired differentiation does not occur and the large particles remain.

Unlike in the prior art, it can be seen that the composition, grain size distribution and morphology of the particles are essential factors for obtaining said osteostimulation by dissolving and disintegration of said particles from their interior, their disappearance and their replacement by osseous tissue.

As the aim is to fill the osseous deficiency as rapidly as possible, it is essential to have a granular material which entirely falls within the claimed grain size fraction. Granules falling outside said fraction do not produce osteostimulation and consequently the sought effect leading to an early osseous formation does not take place.

It can be seen that the invention produces a preferred dissolving of glass, as opposed to reaction mechanisms of bioglasses with a comparable composition and as described in the prior art. Thus, the mechanism described are generally leaching reactions of certain ions on the surface of the glass, without any dissolving of said glass taking place.

Moreover, the rough surface state of the granules, due to their shape characteristics, acts in an agglutinating or imbricating manner and is such that the material is easy to put into place, the particles remaining in place in the cavity and agglutinate to one another, clinging to the osseous cavity walls. Obviously, for particular applications, it is possible to use other placing or installation means.

In conventional manner, the material according to the invention is obtained by firstly preparing a mixture of powders including silica, an alkaline earth oxide (preferably CaO and/or MgO), a carbonate for introducing at least partly the alkali (sodium carbonate being preferably used) and a phosphate or acid phosphate for introducing $P_2O_5$ (preferably $CaHPO_4$).

This mixture is melted and is cast into parts, normally in the form of small cylinders or disks, in relatively solid moulds made from good heat conducting material (e.g. graphite, metal). Annealing can take place. These parts are then reduced to granules by any means making it possible to give rough, cracked particles with numerous sharp angles. Preference is given to the use of crushing and/or grinding, e.g. in the mortar, using a hammer, bar, etc. This is followed by the obtaining of the desired grain size fraction, e.g. by passing through vibrating screens.

It is important that prior to grinding the cast or moulded parts are not in contact with a liquid (e.g. water, acetone), or any other element which could react with the glass. Thus, modifications could then occur of a chemical and/or physical nature, so that the microdefects or microcracks would no longer appear.

EXAMPLES

In order to illustrate the invention, a comparison was made between a material according to the invention and other materials not complying with the indicated conditions.

EXAMPLE 1

This example illustrates the invention.

The starting product was a mixture of powders containing (% by weight):

| | |
|---|---|
| $SiO_2$ | 45% |
| CaO | 24.5% |
| $Na_2O$ | 24.5% |
| $P_2O_5$ | 6% |

This mixture was melted and moulded into small disks (diameter 4 cm, height 1 cm), which were then pulverized with a hammer. A grain size fraction between 300 and 425 μm was then obtained by using screens. The granules obtained were implanted in osseous cavities of the jaw of dogs. These cavities were either due to the extraction of teeth, or were surgically created cavities, or pathological cavities, or periodontal lesions.

The implantation time varied between 1 month and 1 year, after which samples were taken and sections made, followed by preparation for examination. It was firstly found that the particles stayed in place in the cavity. It was also found that the centre of most of the particles in the mass had disintegrated and rapidly dissolved, giving rise to the differentiation of the mesenchymal cells into osteoblasts.

In addition, as from the first month, osseous tissues occurred in these particles covered by an osteoid layer and an osteoblast film permitting the growth of said osseous tissue. A large quantity of these particles are essentially filled with osseous tissue after 3 months, without there being any connection to the osseous tissue obtained by external growth (osteoconduction) from the walls of the osseous cavity.

After one year the cavity was completely filled by osseous tissues. Moreover, there was no inflammation or migration of particles into adjacent tissues.

Figure 1A:
FIG. 1A is a micrographic section of a particle according to the invention after implantation for one month.
Figure 2A:
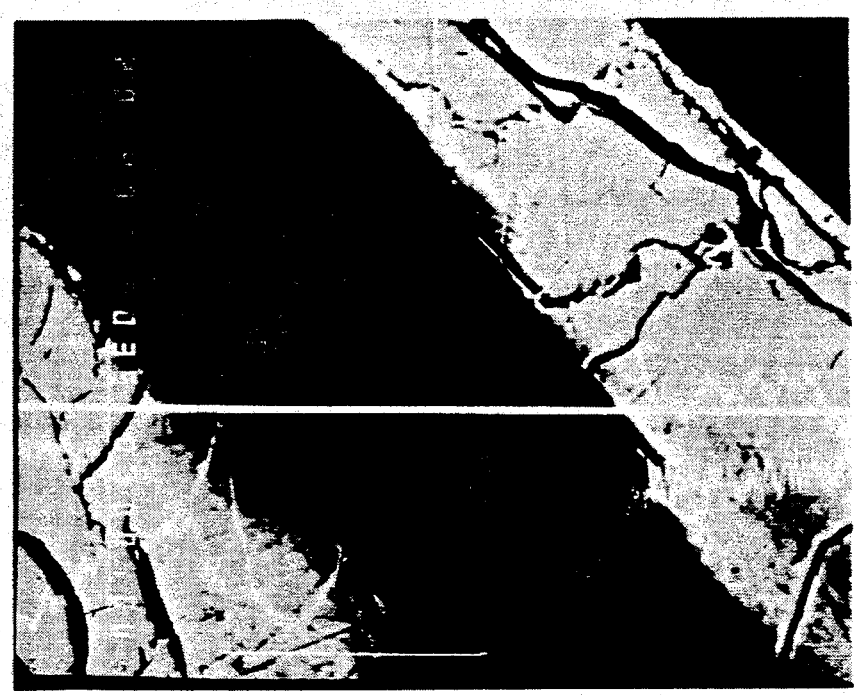
FIG. 2A is a micrographic section of a particle according to the invention after implantation for three months.

FIGS. 1A and 2A are micrographic sections of grains obtained by backscattered electron microscopy, with a superimposing of punctual analyses of the Ca and Si content, performed along a transverse line and indicative for the contents of CaP and silica gel.

Figure 1B:
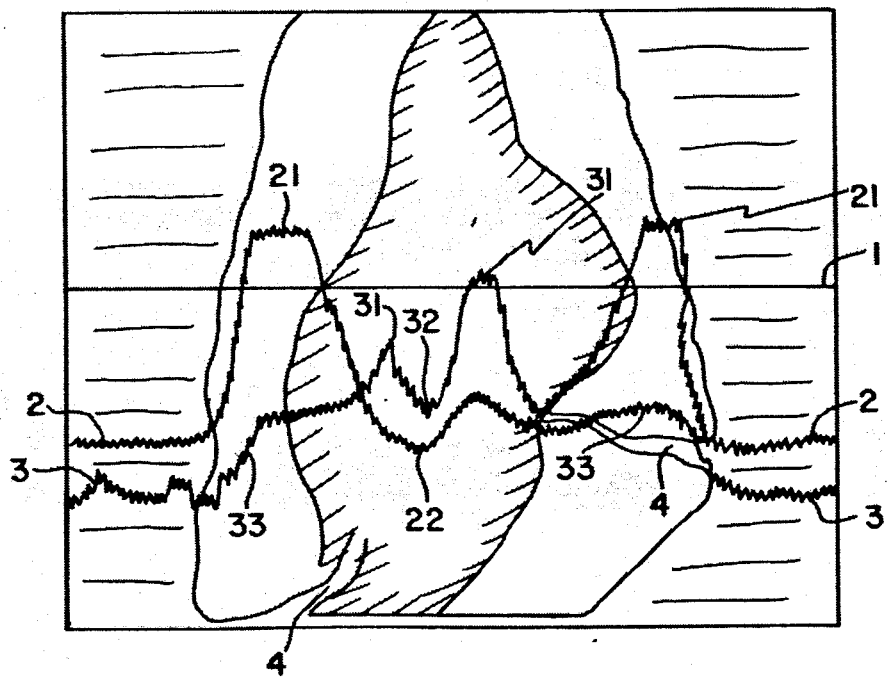
FIG. 1B is an illustration of the particle shown in FIG. 1A.

FIGS. 1A and 1B show a particle according to the invention (magnification×400) after implantation for one month. In light form it is possible to see the CaP-rich external layer and in dark form the partly disintegrated central excavation. Analyses were carried out along the transverse line (1) and along the latter the Ca content is given by curve (2) and the Si content by curve (3). It is possible to see at (21) the CaP-rich outer layer, whereas in the centre of the particle there is a low CaP content (22). There are several zones with respect to the $SiO_2$, namely a zone with a low SiO content (32), during disintegration, and a low CaP layer (22), two zones (33) with low $SiO_2$ contents outside which the CaP layer (21) is forming, two zones (31) containing not yet dissolved silica, whilst at (4) it is possible to see the ducts connecting the excavation to the outside via, initially, surface microdefects.

Figure 2B:
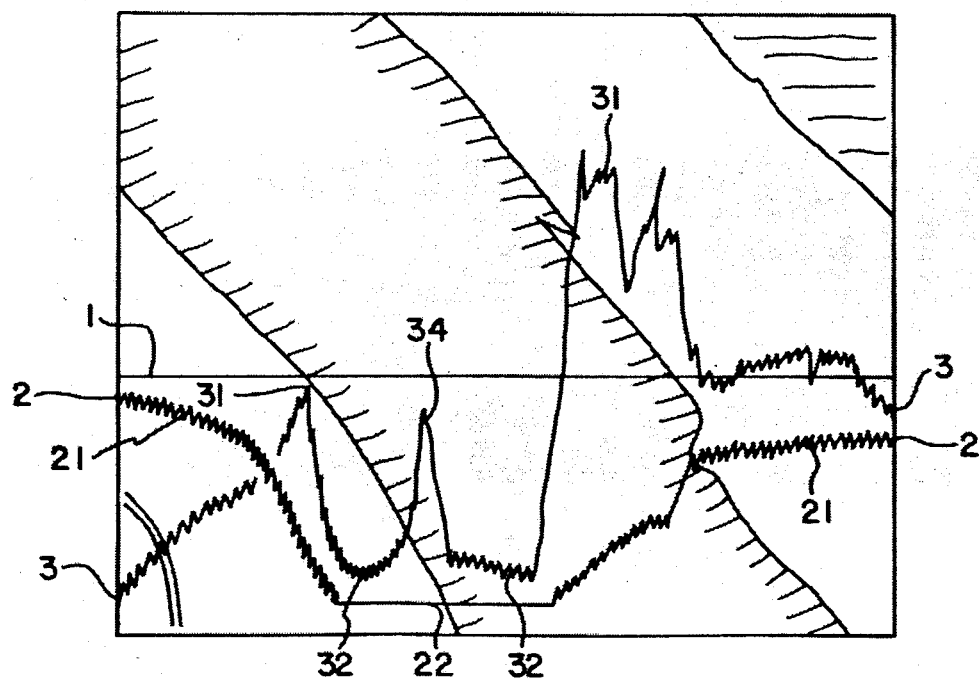
FIG. 2B is an illustration of the particle shown in FIG. 2A.

FIGS. 1A and 2B also show a particle according to the invention after implantation for 3 months. Whereas in FIG. 1 the excavation is forming, it has already formed in FIG. 2. The references have the same meanings as in FIG. 1. However, there is a Si concentration peak (34), which has no particular significance.

Figure 3A:
FIG. 3A is a photomicrograph of a group of particles after three months.
Figure 3B:
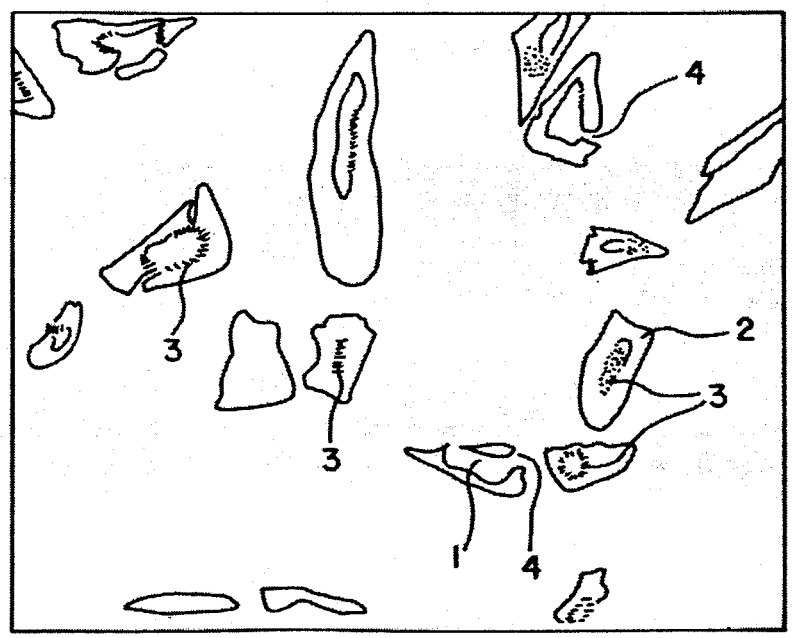
FIG. 3B is an illustration of the particles shown in FIG. 3A.

FIGS. 3A and 3B show a group of particles (magnification×60) after 3 months. In the dark it is possible to see internal excavations (1) in each particle surrounded by the light CaP-rich layer (2). It is possible to see the presence of osseous tissue at (3) in varying quantities. At (4) it is possible to see the ducts linking the excavation to the outside. As stated hereinbefore, no osseous tissue is present in the external medium.

As the section is bidimensional, it could have been taken close to the top of certain particles, which explains the presence in FIGS. 3A and 3B of apparently small and excavation-free particles.

EXAMPLE 2

This example illustrates the imperfect results obtained with a granular material having an excess of large particles (larger than 500 μm). The experimental conditions were identical to those of example 1. The grain size fraction was made larger using 425 to 850 μm screens.

In this case there is an external growth of osseous tissue (osteoconduction) from the osseous cavity wall between the particles and along their surfaces. In the centre of the cavity, the particles are surrounded by fibrous tissues, which consist of densely heaped up collagen fibres. The large particles have no central disintegration with glass resorption or dissolving and substitution by osseous tissue. It is no evident that an ossification of large particles occurs after longer implantation times, because they can be coated and enclosed in osseous tissues formed by osteoconduction, said tissue preventing any increased reaction such as existed at the start of implantation.

EXAMPLE 3

This example illustrates the imperfect results of restoration due to the use of excessively small granules. The experimental conditions are identical to those of example 1, except that the grain size fraction was made smaller using 212 and 300 μm screens.

There is also in this case an external growth of the osseous tissue by osteoconduction from the cavity wall and between the particles, said tissue coating and being joined to the particles. In the centre of the osseous cavity, the differentiation of the precursor cells into osteoblasts does not occur and the particles are surrounded by fibrous tissues prior to disappearing under the action of phagocytic cells.

Only a few large particles reveal a central disintegration with the substitution of their core by the cells described in example 1 and by osseous tissue.

EXAMPLE 4

This example illustrates the poor results obtained with a granular material containing a fluoride, the glass having the following composition (% by weight):

| | |
|---|---|
| $SiO_2$ | 52% |
| CaO | 16% |
| $Na_2O$ | 10% |
| $P_2O_5$ | 6% |
| $CaF_2$ | 16% |

A grain size of 425 to 800 μm was used.

After implantation for 3 months and despite a large grain size, there is an excessively intense inflammatory reaction, which is harmful and which was not observed with the granular material according to the invention. This inflammatory reaction can be attributed to the presence of fluoride.

It can be seen that the granular material according to the invention aids the tissue reaction of osteogenesis by osteostimulation occurring at all points of the osseous deficiency (including the central zone) within the particles, by destroying them and replacing them by osseous tissue and without preventing an osteoconduction, which tends to coat the particles, without destroying them, from the walls of the osseous cavity.

We claim:

1. Process for the formation of osseous tissue for filling an osseous defect or deficiency, comprising introducing particles consisting essentially of an inorganic, non-fluorinated, bioreactive granular material having sharp edges, an irregular profile and surface defects or microcracks into said osseous defect or deficiency in order to cause osteogenesis by osteostimulation, said particles being progressively dissolved internally, by way of said surface defects or microcracks to create a central cavity in which mesenchymal precursor cells are differentiated into osteoblasts, followed by progressive replacement of said particles by osseous tissue, said particles consisting essentially of, by weight:
$SiO_2$ between 40 and 55%;
$Na_2O$ between 10 and 32%;
$P_2O_5$ between 0 and 12%; and
CaO between 10 and 32%;
and having a grain size distribution such that at least 95% of the particles are between 280 and 425 μm.

2. Process according to claim 1, wherein ⅔ of the particles are between 300 and 360 μm.

3. Process according to claim 2, wherein at least 90% of the particles are between 300 and 360 μm.

4. Process according to claim 2 or 3, wherein the particles consist essentially of bioreactive glass having a composition, by weight:
$SiO_2$ between 42 and 48%;
$Na_2O$ between 14 and 28%;
$P_2O_5$ between 0 and 10%; and
CaO between 20 and 29%.

5. Process according to claim 1, 2 or 3, comprising forming said particles by melting together a mixture of inorganic powders containing the constituents of said particles, molding said melted powders and solidifying in the absence of contact with any material reactive with said mixture of powders, and pulverizing said solidified mixture.

6. Process according to claim 4, comprising forming said particles by melting together a mixture of inorganic powders containing the constituents of said particles, molding said melted powders and solidifying in the absence of contact with any material reactive with said mixture of powders, and pulverizing said solidified mixture.

7. Process according to claim 5, wherein said pulverizing takes place with a hammer.

8. Process according to claim 6 wherein said pulverizing takes place with a hammer.

* * * * *

UNITED STATES PATENT AND TRADEMARK OFFICE
CERTIFICATE OF CORRECTION

PATENT NO. : 5,204,106
DATED : April 20, 1993
INVENTOR(S) : Evert Schepers et al It is certified that error appears in the above-indentified patent and that said Letters Patent is hereby corrected as shown below:

On the title page: Item [75] Amend the title page by adding after "Raymond Kempeneers, Mol, Belgium":

--Marcel de Clercq, deceased, late of Rotselaar, Belgium, by Maria M. Van Hoeylandt, legal representative. --

Signed and Sealed this

Seventh Day of December, 1993

Attest:

BRUCE LEHMAN

Attesting Officer     Commissioner of Patents and Trademarks

REEXAMINATION CERTIFICATE (2759th)

United States Patent [19]

Schepers et al.

[11] B1 5,204,106

[45] Certificate Issued  Dec. 26, 1995

[54] PROCESS FOR RESTORING AN OSSEOUS DEFECT OR DEFICIENCY BY FILLING WITH OSSEOUS TISSUE

[75] Inventors: Evert Schepers, Leuven, Belgium; Paul Ducheyne, Bryn Mawr, Pa.; Raymond Kempeneers, Mol, Belgium; Marcel de Clercq, deceased, late of Rotselaar, Belgium, by Maria M. Van Hoeylandt, legal representative

[73] Assignee: FBFC International, S.A., Brussels, Belgium

Reexamination Request:
No. 90/003,508, Jul. 27, 1994

Reexamination Certificate for:
Patent No.: 5,204,106
Issued: Apr. 20, 1993
Appl. No.: 511,303
Filed: Apr. 19, 1990

Certificate of Correction issued Dec. 7, 1993.

[30] Foreign Application Priority Data

Apr. 20, 1989 [FR] France .................. 89 05504

[51] Int. Cl.⁶ .................................................. A61F 2/28
[52] U.S. Cl. ........................ 424/423; 623/16; 424/422
[58] Field of Search ............................ 424/423, 426; 623/16

[56] References Cited

U.S. PATENT DOCUMENTS 4,851,046  7/1989  Low et al. .................. 106/35

*Primary Examiner*—Thurman K. Page

[57] ABSTRACT

Process for the restoration of an osseous defect or deficiency by filling with osseous tissue with the aid of a bioreactive granular material causing an osteostimulation, the particles of said granular material being disintegrated from the inside, dissolved and replaced by osseous tissue, the granular material containing 40 to 55% $SiO_2$, 10 to 32% $Na_2O$, 0 to 12% $P_2O_5$ and 10 to 32% CaO, which has a grain size distribution between 280 and 425 μm, sharp edges, an irregular profile and surface microdefects or microcracks.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

* * * * *